(12) United States Patent
Berry et al.

(10) Patent No.: US 7,596,965 B2
(45) Date of Patent: Oct. 6, 2009

(54) ANESTHETIC GAS RECLAMATION SYSTEM AND METHOD

(75) Inventors: James M. Berry, Nashville, TN (US); Steve Morris, Canton, MS (US)

(73) Assignee: Anesthetic Gas Reclamation, LLC, Nashville, TN (US)

( * ) Notice: Subject to any disclaimer, the term of this patent is extended or adjusted under 35 U.S.C. 154(b) by 319 days.

(21) Appl. No.: 11/432,189

(22) Filed: May 11, 2006

(65) Prior Publication Data

US 2006/0254587 A1 Nov. 16, 2006

Related U.S. Application Data

(60) Provisional application No. 60/680,644, filed on May 13, 2005, provisional application No. 60/682,249, filed on May 18, 2005.

(51) Int. Cl.
*B01D 9/04* (2006.01)
*F25J 3/00* (2006.01)
*F24F 5/00* (2006.01)
*A62B 7/00* (2006.01)

(52) U.S. Cl. .......................... 62/532; 62/617; 62/637; 128/204.16; 128/205.12

(58) Field of Classification Search .................. 62/637, 62/617, 532; 128/200.24, 204.16, 203.25, 128/205.12; 423/235
See application file for complete search history.

(56) References Cited

U.S. PATENT DOCUMENTS 575,714 A 1/1897 Heinzerling
1,040,886 A 10/1912 Claude (Continued)

FOREIGN PATENT DOCUMENTS

WO WO 98/08583 3/1998

(Continued)

OTHER PUBLICATIONS

R. F. Dunn, M. Zhu, B.K. Srinivas and M. M. El-Halwagi (1995), Optimal Design of Energy-Induced Separation Networks for VOC Recovery, *AIChE Symp. Ser.*, 90(303), 74-85, NY: AIChE.

(Continued)

*Primary Examiner*—William C Doerrler
(74) *Attorney, Agent, or Firm*—Gary L. Bush; Mark D. Shelley, II; Andrews Kurth LLP (57) ABSTRACT

A method and system for the fractionation and removal of nitrous oxide and other volatile halocarbon gas components from waste anesthetic gases using liquid oxygen are disclosed. Liquid oxygen is warmed for use in a healthcare facility by cooling and condensing waste anesthetic gases. A cold trap/fractionator is provided wherein selective components of the waste anesthetic gas are collected as a frost on the coils of the cold trap/fractionator by desublimation/deposition and/or condensation/solidification. In a periodic batch process, the collected frost is first thawed and the melted liquids or gases are then collected at various increasing temperatures, thereby separating the nitrous oxide and other halocarbon gas components by their varying melting points. The thawed anesthetic components are collected in separate tanks based on their melting points. Warmed by the waste anesthetic gases in the cold trap/fractionator, the oxygen is supplied to the healthcare facility for its normal uses.

20 Claims, 3 Drawing Sheets

U.S. PATENT DOCUMENTS

| | | | |
|---|---|---|---|
| 3,348,538 A | 10/1967 | Benzel | |
| 3,517,521 A * | 6/1970 | Emerson | 62/637 |
| 3,592,191 A | 7/1971 | Jackson | |
| 3,714,942 A | 2/1973 | Fischel et al. | |
| 3,721,239 A | 3/1973 | Myers | |
| 3,800,793 A | 4/1974 | Marrese et al. | |
| 3,867,936 A | 2/1975 | Kelley | |
| 3,941,573 A | 3/1976 | Chapel | |
| 4,004,585 A | 1/1977 | Boehringer | |
| 4,127,163 A | 11/1978 | Reti | |
| 4,180,066 A | 12/1979 | Milliken et al. | |
| 4,181,508 A * | 1/1980 | Schmid et al. | 95/290 |
| 4,205,095 A | 5/1980 | Pike et al. | |
| 4,219,020 A | 8/1980 | Czajka | |
| 4,246,015 A | 1/1981 | Styring, Jr. | |
| 4,259,303 A | 3/1981 | Nakaji et al. | |
| 4,265,239 A | 5/1981 | Fischer, Jr. et al. | |
| 4,281,518 A | 8/1981 | Muller et al. | |
| 4,291,689 A | 9/1981 | Hay | |
| 4,312,339 A | 1/1982 | Thompson, Sr. | |
| 4,378,984 A * | 4/1983 | Cheng et al. | 62/637 |
| 4,447,462 A | 5/1984 | Tafuri et al. | |
| 4,451,273 A | 5/1984 | Cheng et al. | |
| 4,527,558 A | 7/1985 | Hoenig | |
| 4,538,605 A | 9/1985 | Gedeon et al. | |
| 4,609,388 A | 9/1986 | Adler et al. | |
| 4,633,890 A | 1/1987 | Carden | |
| 4,653,493 A | 3/1987 | Hoppough | |
| 4,676,239 A | 6/1987 | Humphrey | |
| 4,755,201 A | 7/1988 | Eschwey et al. | |
| 4,832,042 A | 5/1989 | Poppendiek et al. | |
| 4,895,172 A | 1/1990 | Lindkvist | |
| 4,905,685 A | 3/1990 | Olsson et al. | |
| 4,928,685 A | 5/1990 | Gray | |
| 4,949,714 A | 8/1990 | Orr | |
| 5,033,464 A | 7/1991 | Dlcastilho | |
| 5,044,361 A | 9/1991 | Werner et al. | |
| 5,044,363 A | 9/1991 | Burkhart | |
| 5,046,491 A | 9/1991 | Derrick | |
| 5,046,492 A | 9/1991 | Stackhouse et al. | |
| 5,062,270 A | 11/1991 | Haut et al. | |
| 5,152,812 A | 10/1992 | Kovach | |
| 5,205,843 A | 4/1993 | Kaschemekat et al. | |
| 5,253,641 A | 10/1993 | Choate | |
| 5,311,862 A | 5/1994 | Blasdell et al. | |
| 5,323,623 A | 6/1994 | Carns et al. | |
| 5,339,642 A | 8/1994 | Laukhuf | |
| 5,345,928 A | 9/1994 | Lindkvist | |
| 5,370,110 A | 12/1994 | Corn | |
| 5,398,675 A | 3/1995 | Henkin et al. | |
| 5,419,317 A | 5/1995 | Blasdell et al. | |
| 5,450,728 A | 9/1995 | Vora et al. | |
| 5,482,033 A | 1/1996 | Engle et al. | |
| 5,507,282 A | 4/1996 | Younes | |
| 5,520,169 A | 5/1996 | Georgieff et al. | |
| 5,568,910 A | 10/1996 | Koehler et al. | |
| 5,676,133 A | 10/1997 | Hickle et al. | |
| 5,678,540 A | 10/1997 | Kock et al. | |
| 5,694,924 A | 12/1997 | Cewers | |
| 5,715,813 A | 2/1998 | Guevrekian | |
| 5,740,682 A | 4/1998 | Lavie | |
| 5,759,504 A | 6/1998 | Kanno et al. | |
| 5,769,072 A | 6/1998 | Olsson et al. | |
| 5,819,555 A | 10/1998 | Engdahl | |
| 5,928,411 A | 7/1999 | Falb et al. | |
| RE36,460 E | 12/1999 | Klatz et al. | |
| 6,030,591 A | 2/2000 | Tom et al. | |
| 6,076,524 A | 6/2000 | Corn | |
| 6,080,226 A | 6/2000 | Dolan et al. | |
| 6,082,133 A | 7/2000 | Barclay et al. | |
| 6,131,571 A | 10/2000 | Lampotang et al. | |
| 6,134,914 A | 10/2000 | Eschwey et al. | |
| 6,158,434 A | 12/2000 | Lugtigheid et al. | |
| 6,206,002 B1 | 3/2001 | Lambert | |
| 6,237,596 B1 | 5/2001 | Bohmfalk | |
| 6,328,036 B1 | 12/2001 | Emtell et al. | |
| 6,357,437 B1 | 3/2002 | Jacques | |
| 6,374,635 B1 | 4/2002 | Hayakawa et al. | |
| 6,405,539 B1 | 6/2002 | Stach et al. | |
| 6,475,266 B2 | 11/2002 | Hayashi et al. | |
| 6,488,028 B1 | 12/2002 | Lambert | |
| 6,490,883 B2 * | 12/2002 | Trembley et al. | 62/637 |
| 6,513,345 B1 | 2/2003 | Betting et al. | |
| 6,536,430 B1 | 3/2003 | Smith | |
| 6,729,329 B2 * | 5/2004 | Berry | 128/204.16 |
| 6,736,140 B1 | 5/2004 | Baczkowski | |
| 6,776,158 B1 | 8/2004 | Anderson et al. | |
| 6,863,067 B2 | 3/2005 | Loncar | |
| 2003/0185735 A1 | 10/2003 | Hotta et al. | |
| 2005/0155380 A1 * | 7/2005 | Rock | 62/617 |
| 2006/0254586 A1 | 11/2006 | Berry et al. | |
| 2006/0254589 A1 | 11/2006 | Berry et al. | |
| 2006/0254590 A1 | 11/2006 | Berry et al. | |

FOREIGN PATENT DOCUMENTS

WO     WO 01/24858     4/2001

OTHER PUBLICATIONS

U.S. Appl. No. 11/266,966, filed Nov. 4, 2005, Berry et al.
Brown AC, Canosa-Mas CE, Parr AD, et al.: Tropospheric lifetimes of halogenated anaesthetics. Nature 1989; 341: 635-637.
Langbein T, Sonntag H, Trapp D, et al.: Volatile anaesthetics and the atmosphere: atmospheric lifetimes and atmospheric effects of halothane, enflurane, isoflurane, desflurane and sevoflurane. Br J Anaesth 1999; 82: 66-73.
McCulloch, A.: Letter to Editor regarding Langbein, et al. 1999 paper. Br J Anaesth 2000; 84 (4): 534-36.
Written Opinion of International Search Authority for PCT/US2006/18416 mailed on Sep. 24, 2007.
Examiner's First Office Action mailed Jul. 17, 2008 in connection with U.S. Appl. No. 11/266,966.
Applicant's Response to First Office Action filed Nov. 17, 2008 in connection with U.S. Appl. No. 11/266,966.
Examiner's Second Office Action mailed Dec. 30, 2008 in connection with U.S. Appl. No. 11/266,966.
Examiner's First Office Action mailed Oct. 10, 2008 in connection with U.S. Appl. No. 11/432,192.
Applicant's Response to First Office Action filed Apr. 9, 2009 in connection with U.S. Appl. No. 11/432,192.
Applicant's Supplemental Response to First Office Action filed Apr. 10, 2009 in connection with U.S. Appl. No. 11/432,192.
Examiner's First Office Action mailed Oct. 15, 2008 in connection with U.S. Appl. No. 11/432,152.
Applicant's Response to First Office Action filed Apr. 14, 2009 in connection with U.S. Appl. No. 11/432,152.

* cited by examiner

ANESTHETIC GAS RECLAMATION SYSTEM AND METHOD

CROSS REFERENCE TO RELATED APPLICATION

This application is based upon provisional applications 60/680,644 filed on May 13, 2005 and 60/682,249 filed on May 18, 2005, the priorities of which are claimed. On Nov. 4, 2005. Applicants filed related non-provisional application 11/266.966, which claims the benefit of U.S. provisional patent application 60/680,644 filed on May 13, 2005. On 05/11/2006. Applicants filed related non-provisional application 11/432,152, which claims the benefit of U.S. provisional patent application 60/680,644 filed on May 11, 2006. On May 11, 2006, Applicants filed related non-provisional application 11/432,192, which claims the benefit of U.S. provisional patent application 60/680,644 filed on May 13, 2005.

BACKGROUND OF THE INVENTION

1. Field of the Invention

This invention concerns treatment of waste anesthetic gas. In particular the invention pertains to the removal and reclamation of nitrous oxide, fluoro-ethers, and other halocarbons from waste anesthetic gas of a healthcare facility before the gas is discharged to the atmosphere in order to decrease atmospheric pollution.

2. Description of the Prior Art

The administration of anesthesia in surgical and other healthcare facilities creates significant quantities of waste anesthetic gases. Currently these gases are scavenged, diluted with air in a system of dedicated pipes, and then vented to the atmosphere outside the building. The average composition of the waste gases is estimated to be (in percent volume) 25-32 percent oxygen, 60-65 percent nitrogen, 5-10 percent nitrous oxide, and 0.1-0.5 percent other volatile halocarbons, including fluoro-ethers such as isoflurane, desflurane and sevoflurane.

The halocarbons (primarily halogenated ethers) represent an increasingly significant source of environmental concern, because other halocarbon emissions have recently been reduced by legislative and other initiatives. These compounds (similar to refrigerants Freon-12® and others) can contribute to ozone depletion and environmental warming. Although it is anticipated that regulation of these emissions will occur in the near future, currently no such regulation exists.

Several techniques have been employed to treat waste anesthetic gases. U.S. Pat. No. 4,259,303 describes treating laughing gas with a catalyst. Adsorption of anesthetic gases by charcoal granules is described in U.S. Pat. No. 5,044,363. Destruction of anesthetic gases by heating in the presence of a catalyst is described in U.S. Pat. Nos. 5,759,504 and 6,134,914 issued to Eschwey et al. describes a process for separating xenon from exhaled anesthetic gas, and U.S. Pat. No. 6,729,329 issued to Berry describes a method for removing halocarbons from waste anesthetic gas.

3. Identification of Objects of the Invention

A primary object of the invention is to provide an economical system and method for removing fluoro-ethers and other volatile halocarbons from waste anesthetic gases from a surgical facility before such gases are vented to the atmosphere.

Another object of the invention is to provide an economical system and method for removing nitrous oxide from waste anesthetic gases from a surgical facility before such gases are vented to the atmosphere.

Another object of the invention is to provide an economical system and method for substantially preventing the atmospheric venting of fluoro-ethers and other volatile halocarbons of waste anesthetic gases while eliminating the need of prior art catalysts, charcoal granules and heating techniques.

Another object of the invention is to provide an economic system and method for separating various removed nitrous oxide, fluoro-ethers, and other volatile halocarbon components based on their physical characteristics.

Another object of the invention is to provide an economical system and method which increases a healthcare facility's overall energy efficiency by utilizing existing liquefied gas storage and delivery systems.

Another object of the invention is to provide an economical system and method which minimizes the impact of reclamation system installation on the healthcare facility by utilizing existing liquefied gas storage and delivery systems.

Another object of the invention is to provide a system and method which requires minimal additional investment for a healthcare facility to implement.

Another object of the invention is to provide a system and method which reclaims and allows re-distillation and/or reuse of a large percentage of the nitrous oxide and/or anesthetic halocarbons used in the facility.

Another object of the invention is to provide a system and method which reduces anesthetic-related halocarbon emissions from a healthcare facility into the atmosphere by about 99 percent or more.

SUMMARY OF THE INVENTION

The objects identified above, as well as other advantages and features are preferably embodied in a system and method which uses cold trap or liquid-air trap technology, but more specifically, a batch-mode frost fractionation process such that the temperature and pressure of the fluoro-ethers and other anesthetic halocarbons are lowered to a point where the vapors collect as frost on internal cooling surfaces in a cold trap/fractionator through desublimation (deposition). In other words, the fluoro-ethers and other anesthetic halocarbon components in the waste anesthetic gas are solidified through refrigeration onto cooling coils in a heat exchanger to remove the components from the effluent gas. The source of refrigeration is preferably liquid oxygen, which is available at surgical facilities, such as hospitals or outpatient clinics, and must generally be warmed for ordinary use. However, other liquefied gases, such as liquid nitrogen, etc., are also commonly found at healthcare facilities and may be equally used as a source of refrigeration. The cold trap/fractionator is periodically cycled through a thawing stage during which the cooling surfaces, caked with frost gas components trapped from the waste anesthetic gas passing thereby, are slowly warmed to sequentially separate and collect the trapped components. At sufficiently high pressures (i.e., typically atmospheric pressure and above), the trapped fluoro-ethers and other anesthetic halocarbon components melt and the liquefied components are drained into separate tanks, depending on their physical characteristics. At sufficiently low pressures (i.e., typically below atmospheric pressure), the trapped fluoro-ethers and other anesthetic halocarbon components do not liquefy but rather sublime directly into the vapor phase. These reclaimed anesthetic vapors are preferably collected via a gaseous anesthetic collection system for further processing. The remainder of the anesthetic gas is preferably vented to atmosphere.

BRIEF DESCRIPTION OF THE DRAWINGS

The invention is described in detail hereinafter on the basis of the embodiments represented in the accompanying figures, in which.

DESCRIPTION OF THE PREFERRED EMBODIMENT OF THE INVENTION

Figure 1:
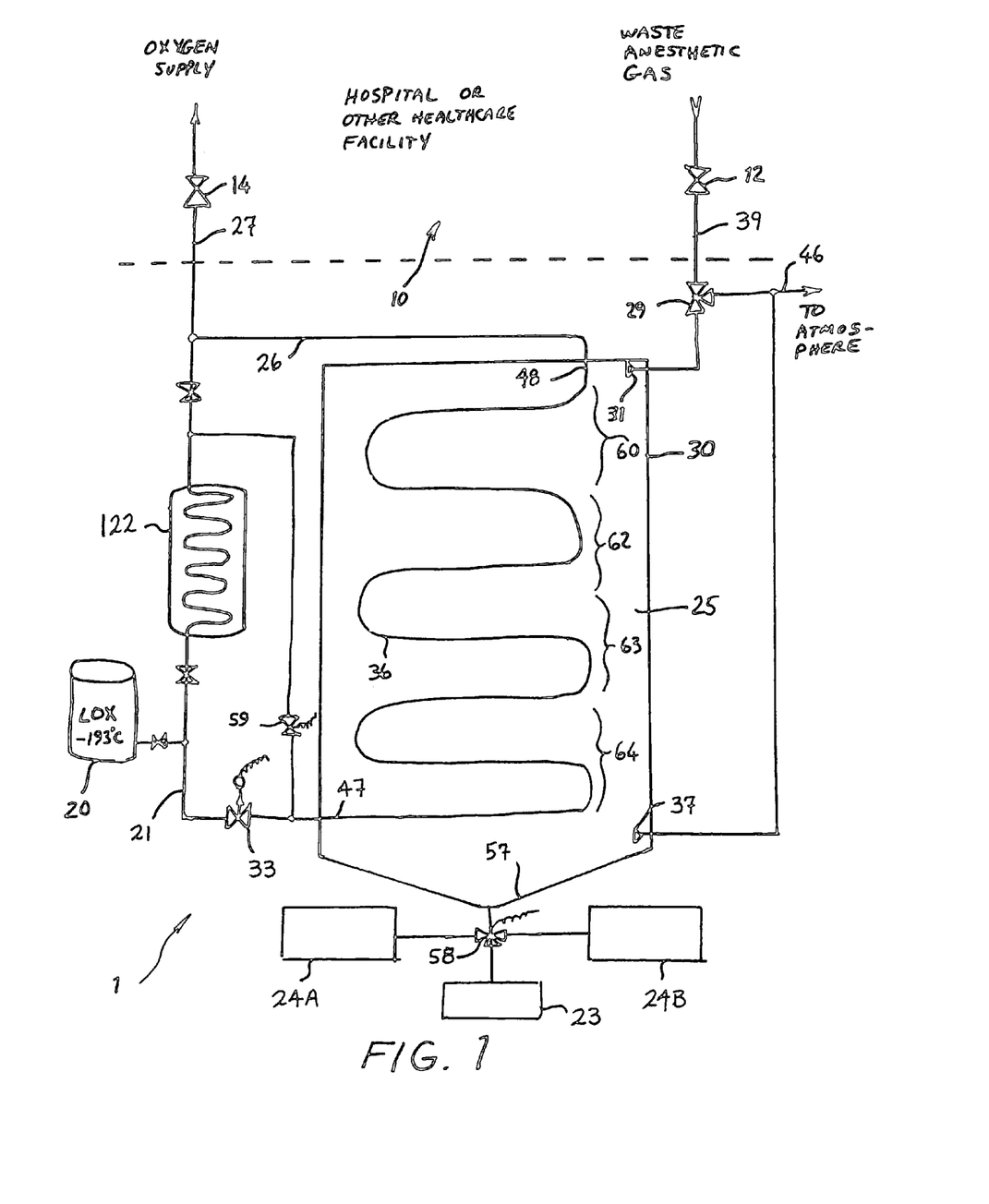
FIG. 1 illustrates in schematic form the process and system by which fluoro-ethers and other volatile halocarbon gas components of waste anesthetic gases are separated therefrom and subsequently fractionated by sequential thawing and collection of the resultant liquid halocarbon prior to venting of the waste anesthetic gases to the atmosphere, using as a heat sink for the process a source of liquefied oxygen.

FIG. 1 illustrates the reclamation system 1 according to one embodiment of the invention for use at a hospital, a surgical facility, or other healthcare facility 10. Waste anesthetic gas is collected and passed through a valve 12 in facility 10 to a waste gas flow line 39. A flow line 27 to supply oxygen to the facility 10 preferably includes a valve 14 to which downstream oxygen service lines inside the hospital 10 are fluidly connected. A source of liquid oxygen is schematically illustrated by tank 20 which preferably exists near the healthcare facility 10. Currently, hospitals and other healthcare facilities 10 pass the liquid oxygen through a heat exchanger 122 to raise the temperature of the liquid oxygen (about −193° C.) to room temperature (about 25° C.) before reaching the facility 10 via flow line 27. Normally, liquid oxygen is warmed using heat exchangers 122 located near each tank 20 which expose the liquid oxygen to ambient air temperature. The warmed oxygen gas is then applied by flow line 27 and valve 14 to service lines (not shown) for distribution to the point of patient use within the healthcare facility 10.

In one embodiment of the invention, as illustrated in FIG. 1, a cold trap/fractionator 25, which includes an enclosure 30 containing cooling coils 36 therein, serves as a heat exchanger. The internal volume of the cooling coils 36 is fluidly isolated from the remaining volume of the enclosure 30, but the two volumes are thermally/conductively coupled. The cold trap/fractionator 25 promotes heat exchange from waste anesthetic gas in enclosure 30 to liquid oxygen in cooling coils 36. The waste anesthetic gas is provided from the facility 10 by flow line 39, and the liquid oxygen is provided by the liquid oxygen source 20 by flow line 21. Enclosure 30 preferably is of double-walled construction, which provides improved insulation from ambient conditions and thus facilitates heat exchange solely between the waste anesthetic gas and the liquid oxygen.

The source flow line 21 for liquid oxygen is preferably fluidly connected to the inlet 47 of the condensing coils 36 by a thermostatic control valve 33. The outlet 48 of the cooling coils is fluidly connected by flow line 26 to flow line 27 for oxygen supply to the facility 10. The existing heat exchanger 122 used to warm the liquid oxygen preferably remains in place fluidly connected in parallel with cold trap/fractionator 25 between liquid oxygen tank 20 and oxygen flow line 27 to warm the oxygen when facility oxygen demand is greater than the demand of the cold trap/fractionator 25, when the cold trap/fractionator 25 is operating in its thaw cycle as described below, or when the cold trap/fractionator 25 is out of service, such as for maintenance or repair.

A waste anesthetic gas flow line 39 and cut-out valve 12 fluidly connect to collection flow lines (not shown) in the facility 10. Preferably, waste anesthetic gas flow line 39 is selectively fluidly coupled to an inlet 31 of enclosure 30 or an atmospheric discharge vent 46 by a 3-way bypass valve 29. During normal operations, flow line 39 is directed only to the inlet 31 of enclosure 30 by the 3-way selector valve 29. The waste anesthetic gas flows through enclosure 30 of cold trap/fractionator 25 towards outlet fitting 37, during which gas components are removed by desublimation (deposition) onto the cooling coils 36, and from fitting 37 the waste anesthetic gas flows to the atmosphere via vent 46. The waste anesthetic gas flow line 39 is preferably only directly aligned to the atmospheric discharge vent 46, bypassing the cold trap/fractionator 25, for system maintenance, repair, or when it is desirable for the reclamation system not to be in use.

The waste anesthetic gas (generally containing nitrogen, oxygen, nitrous oxide, nitrous oxide, water vapor and fluoro-ethers) generally enters through flow line 39 at about 20-30° C. with a relative humidity ranging between 10 to 60 percent. The waste anesthetic gas may also contain trace lubricating oil vapor from the vacuum pumps (not shown). Liquid oxygen (about −193° C.), enters the cold trap/fractionator 25 at the inlet 47 to cooling coils 36, while the waste anesthetic gas (about 20-30° C.) enters the enclosure 30 of the cold trap/fractionator 25 at inlet fitting 31. This countercurrent heat exchanger arrangement results in a temperature gradient where the top of the cold trap/fractionator 25 is the warmest and where the bottom of the cold trap/fractionator 25 is the coldest. The upper region 60 of the cooling coils 36 of the cold trap/fractionator 25 cools the waste anesthetic gas from about 20° C. to about −5° C. to extract water vapor as frost on the coils 36. The upper middle region 62 of the cooling coils 36 next cools the waste anesthetic gas to extract sevoflurane at about −60° C. by desublimation/deposition onto the coils 36. Next, the lower middle region 63 extracts nitrous oxide by desublimation/deposition at about −90° C., and finally the lower region 64 of the cooling coils 36 extracts isoflurane and desflurane between −100° C. and −110° C. by desublimation/deposition onto the coils 36. Desublimation/deposition of the anesthetic component directly onto coils 36 generally occurs only at low temperatures and pressures. For example, nitrous oxide desublimates/deposits at temperatures and pressures below its triple point of −90° C. and 0.88 bar. Alternatively, one or more of the anesthetic components may condense as a liquid and solidify onto coils 36 at a temperature region 62, 63, 64 corresponding to their individual physical characteristics.

The remainder of waste gas (mostly nitrogen and oxygen at about −110° C.) is then exhausted to the atmosphere via line 46 or further processed, for example, by existing catalytic technologies. The liquid oxygen, which enters the cold trap/fractionator 25 at about −193° C., exits the cold trap/fractionator 25 at about 0° C. The oxygen may be further warmed by a subsequent process or mixed with warmer oxygen effluent from heat exchanger 122 to reach room temperature or other appropriate temperature for healthcare facility use.

The cold trap/fractionator 25 is periodically cycled through a thaw process. During the thaw cycle, the cold trap/fractionator 25 is slowly warmed to about 0° C. to defrost the cooling coils 36. Warming is achieved by reducing or securing the flow of liquid oxygen through cooling coils 36 by thermostatic control valve 33 and allowing the cold trap/fractionator 25 to warm to room temperature by heat transfer with its surroundings. In an alternate embodiment, warm oxygen from heat exchanger 122 may be directed through the cooling coils 36 by opening valve 59 to increase the thaw rate. In yet a third embodiment, another fluid (not shown) may be directed through cooling coils 36 to achieve a controlled thaw.

The bottom end 57 of enclosure 30 is funnel-shaped and acts as a hopper. The lowest point preferably drains into a 4-way selector valve 58, which in turn is fluidly coupled to three drain tanks 23, 24A, 24B. At sufficiently high pressures (i.e., typically atmospheric pressure and above), the solidified anesthetic components melt as removable liquids. Therefore, as the temperature warms past about −100° C., desflurane (melting point of approximately −108° C.) and isoflurane (melting point of approximately −103° C.) melt from the lower region 64 of cold trap/fractionator 25 and collect in the hopper 57. Selector valve 58 is concurrently aligned to allow the liquid desflurane and isoflurane to gravity feed into the low melting point collection tank 24B. Alternatively, desflurane or isoflurane could be collected in tank 24A with sevoflurane. While the liquid desflurane and isoflurane are preferably collected in the same tank 24B, two separate collection tanks (not shown), one for each component, could also be used.

As the cold trap/fractionator warms past −90° C., the trapped nitrous oxide (melting point of approximately −90° C.) melts from the lower middle region 63 of cold trap/fractionator 25 and collects in the hopper 57. Selector valve 58 is concurrently aligned to allow the liquid nitrous oxide to gravity feed into mid melting point collection tank 24A. Alternatively, nitrous oxide could be collected in tank 24B with desflurane and/or isoflurane or a separate tank (not shown) could be used to collect the nitrous oxide. As the temperature warms further still, the selector valve 58 is positioned to align hopper 57 with the mid melting point collection tank 24A. When the temperature exceeds about −65° C., sevoflurane (melting point of approximately −67° C.) melts from the upper middle region 62 of the cooling coils 36 of the cold trap/fractionator 25, collects in the hopper 57, and drains by gravity into tank 24A. Likewise, as the cold trap/fractionator 25 warms past freezing, the water vapor frost will melt from the upper region 60 and be routed by selector valve 58 into the high melting point collection tank 23. Containers 24A and 24B may be cooled and/or pressurized to maintain the collected fluoro-ethers at low vapor pressure to minimize evaporative losses. The containers 23, 24A, and 24B may be of any suitable strength and/or capacity, for example, 55 gallon steel drums.

Thus, the fluoro-ethers are fractionated by desublimation/deposition and/or condensation/solidification as they are removed from the waste anesthetic gas and then discretely recovered by selectively thawing the deposited frosts. In addition to fluoro-ethers, this reclamation method and system may also be used to remove other suitable gas components from the waste gas stream. Furthermore, while this embodiment describes fractionation of the anesthetic components using three general melting point ranges, a larger number of melting point ranges or selectively narrower melting point ranges may be used as appropriate.

For a large hospital 10 having between 20-30 operating rooms, it is estimated that waste anesthetic gas mass flow rate via flow line 39 ranges between 500-1,000 1/min (14-35 scf/min) at a less than 2 psig. At a temperature of approximately −150° C., oxygen gas inflow through flow line 21 to the same large hospital 10 averages 1,000-2,000 1/min (60-100 scf/min) at a pressure of about 50 psig. Based on these flow rates, the cold trap/fractionator 25 is preferably designed and arranged to have a capacity to trap 8 liters (10 kg) of frozen halocarbon gases and 20 liters (20 20kg) of frozen water prior to the required thawing cycle. Alternatively, the waste gas system may operate at an increased pressure, for example, up to about 50 psig, for increased efficiency, however, desublimation/deposition of the anesthetic components will probably not be possible at this increased pressure. A method and apparatus to enhance anesthetic condensation using a compression stage have recently been disclosed by Berry et al. in co-pending application 11/432,152, entitled "Method and Apparatus for Anesthetic Gas Reclamation With Compression Stage." This co-pending application, filed on May 11, 2006, is Incorporated herein by reference.

This application is based upon provisional applications 60/680,644 filed on May 13, 2005 and 60/682,249 filed on May 18, 2005, the priorities of which are claimed.

This application is based upon provisional applications 60/680,644 filed on May 13, 2005 and 60/682,249 filed on May 18, 2005, the priorities of which are claimed.

Because the oxygen demand for facility 10 can be diurnally variable, the reclamation system 1 according to a preferred embodiment of the invention uses a thermostatically controlled bypass valve 59, in conjunction with the existing heat exchanger 122 and the cold trap/fractionator 25, to maintain optimal oxygen supply temperatures at flow line 27 to the facility 10. A control system (not shown), which comprises flow measurement devices, temperature measurement devices, and/or pressure measurement devices (not shown), is employed to automatically control the setting of thermostatic control valves 33, 59. The control system also contains circuitry to control the thaw cycle, which additionally controls bypass valve 59 and selector valve 58 as appropriate. As the selection measurement devices and the design and construction of control systems are well known in the art, they are not discussed further herein. U.S. Pat. No. 6,134,914 issued to Eschwey et al. and U.S. Pat. No. 6,729,329 issued to Berry are incorporated herein by reference.

The reclamation system 1 described above requires only three additional components for implementation at most healthcare facilities 10: (1) a cold trap/fractionator 25 located near a source of liquid oxygen 20 and connected thereto, (2) piping to deliver the waste anesthetic gases to the cold trap/fractionator 25, and (3) drain tanks 23, 24A, and 24B to collect water and fractionated liquid halocarbons from the reclamation system 1. In addition to liquefied oxygen, other commonly available liquefied gases, such as liquid nitrogen, etc., may be used as a source of refrigeration. Piping 39 for anesthetic waste gas delivery to the system 1 can be designed for relatively low pressures, although oxygen content of this stream could be as high as 40-50 percent. However, a high percentage of oxygen in the waste gas flow line 39 requires oxygen-clean installation precautions. All oxygen pathways are preferably grease free and oxygen safe per the National Fire Protection Association standard 99 (NFPA 99). The oxygen pathway through heat exchanger 122 must also be fail safe to allow full oxygen flow to the facility 10. Thus, in a preferred embodiment, oxygen from tank 20 flows through heat exchanger 122 to flow line 27 and facility 10 during a loss of power while thermostatic bypass valve 33 fails shut to prevent oxygen flow through cold trap/fractionator 25.

Figure 2:
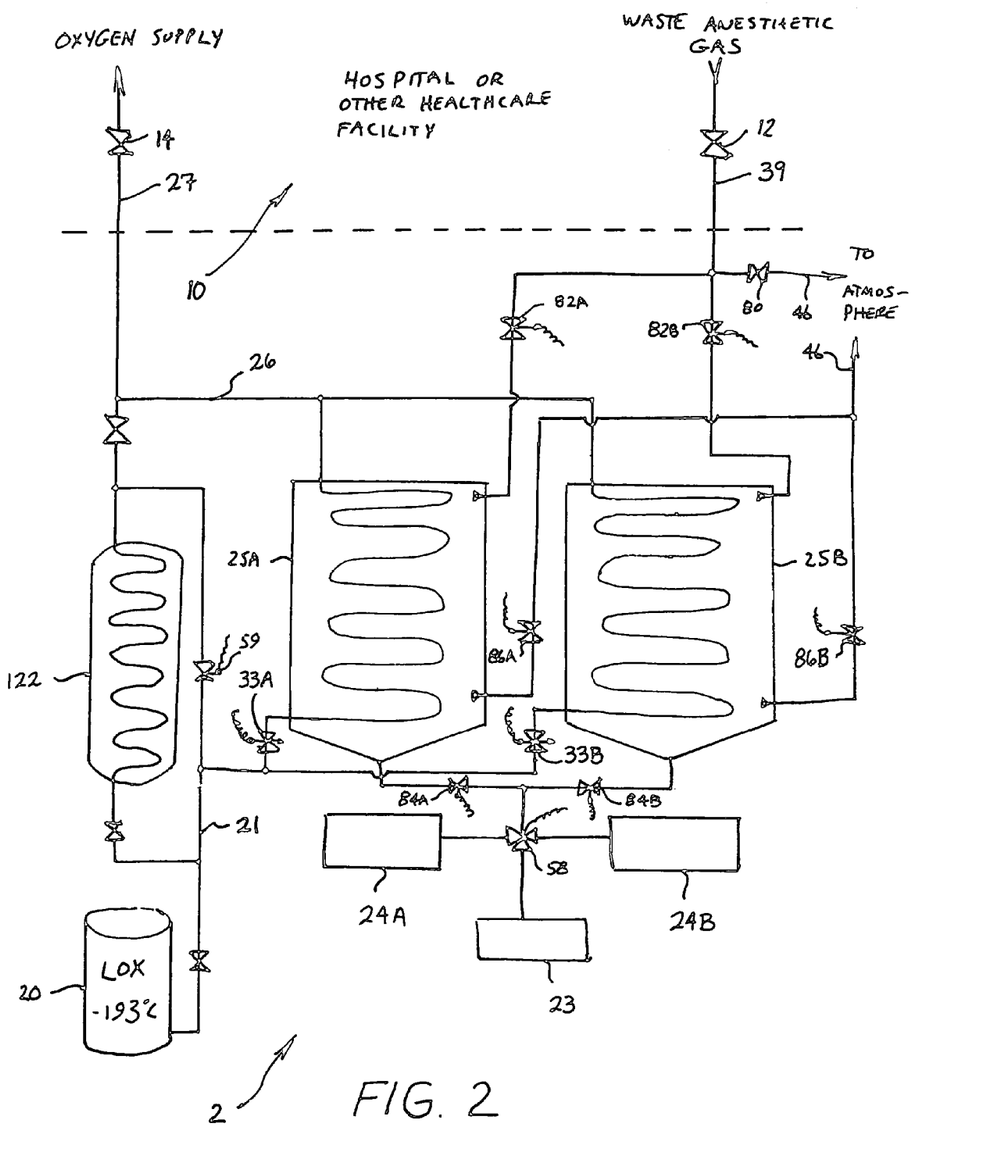
FIG. 2 illustrates in schematic form an alternative embodiment including a parallel of two or more cold trap/fractionators.

FIG. 2 illustrates an alternative embodiment of the invention. The reclamation system 2 is substantially identical to reclamation system 1 of FIG. 1, except that system 2 comprises two cold trap/fractionators 25A, 25B configured in a parallel arrangement. When the first cold trap/fractionator 25A is in the thaw cycle, the second cold trap/fractionator 25B operates in the cold trap mode, and vice versa. This configuration allows for continuous processing of the anesthetic waste gas. In a variation of this alternative embodiment, a third cold trap/fractionator (not shown) may be added in parallel for redundancy.

As shown in FIG. 2, each cold trap/fractionator 25A, 25B has its own respective thermostatic control valve 33A, 33B. Each cold trap/fractionator 25A, 25B also has an associated waste gas supply valve 82A, 82B which operate in coordination with waste gas bypass valve 80 to direct waste anesthetic gas flow to the cold trap/fractionator 25A, 25B currently operating in the trap cycle. If desired, each cold trap/fractionator 25A, 25B may also have a waste gas vent valve 86A, 86B. Additionally, drain valves 84A, 84B cooperate with selector valve 58 to drain the cold trap/fractionator 25A, 25B currently operating in the thaw mode. The operation of the reclamation system 2, including the positions of valves 33A, 33B, 82A, 82B, 84A, 84B, 86A, 86B, 58, and 59, is preferably coordinated by a control system (not shown). Because the design and construction of control systems are well known in the art, they are not discussed further herein.

Figure 3:
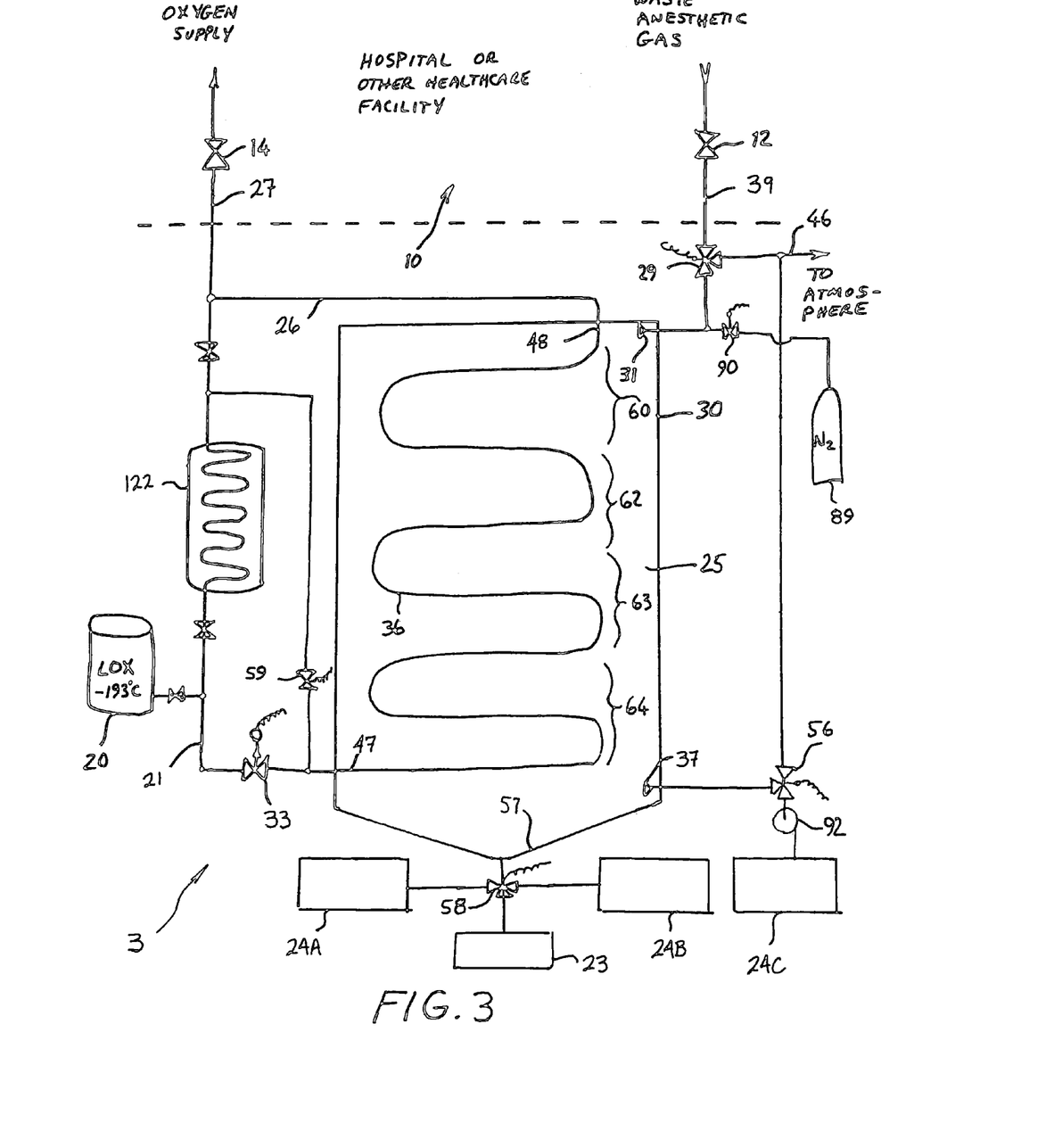
FIG. 3 illustrates in schematic form an alternative embodiment of the reclamation system of FIG. 1 including means to collect trapped components of the waste anesthetic gas which evaporate from the liquid phase or sublime directly into the vapor phase.

FIG. 3 illustrates a third embodiment of the invention. At sufficiently low pressures (i.e., typically below atmospheric pressure), one or more of the solidified anesthetic components may sublime directly into the vapor phase. Alternatively, one or more of the solidified anesthetics may evaporate during the thaw cycle, depending on the operational temperature and pressure of the cold trap/fractionator 25. Reclamation system 3 is substantially identical to the reclamation system 1 of FIG. 1, except that system 3 is arranged and designed to recapture anesthetic gases trapped from the waste anesthetic gas stream which have sublimed or evaporated during the thawing cycle.

As shown in FIG. 3, reclamation system 3 includes additional equipment, such as a gaseous anesthetic collection tank 24C, a 3-way collection valve 56, an optional vacuum pump 92 and an optional source of nitrogen or other gas 89 with an accompanying isolation valve 90. Collection valve 56, 3-way selector valve 29, and nitrogen isolation valve 90 (if present) are all preferably controlled by the control system (not shown) previously described for use with embodiment 1 of FIG. 1. During the trap mode of operation, collection valve 56 is positioned so that outlet fitting 37 is fluidly coupled to the atmospheric discharge vent 46. Waste anesthetic gas enters the cold trap/fractionator 25 through inlet 31, passes over cooling coils 36 to trap water vapor, nitrous oxide, fluoro-ethers, and other volatile halocarbons, and then passes to the atmosphere through outlet 37, nitrous oxide collection valve 56, and vent line 46. Because fluoro-ethers and other halocarbon anesthetics are generally more dense then either nitrogen or oxygen, these sublimated anesthetic gases collect below any existing air (mostly nitrogen and oxygen) in the cold trap/fractionator 25. Thus, during the thaw cycle, these sublimed anesthetic gases collect just above any liquid at the bottom of enclosure 30. Collection valve 56 is aligned so that outlet fitting 37 is fluidly coupled with gaseous anesthetic collection tank 24C. Solid anesthetic components which melt as a liquid, rather than sublime as a vapor, are collected via hopper 57, selector valve 58, and collection tanks 24A, 24B as previously disclosed.

Sublimed anesthetic gas is reclaimed by one of several methods. First, the sublimed anesthetic gas disposed just above any liquid level at the bottom of enclosure 30 may be displaced and collected in tank 24C by using a nitrogen blanket. Nitrogen gas or another suitable blanket gas is allowed to flow through nitrogen isolation valve 90 and into the top of cold trap/fractionator 25 through inlet fitting 31. The 3-way selector valve 29 is shut to isolate enclosure 30 from vent 46 and waste anesthetic gas entering from facility 10. As the nitrogen gas flows into the top of cold trap/fractionator 25, it forces the denser anesthetic gas to flow out of cold trap/fractionator 25, through outlet fitting 37, and into collection tank 24C. Nitrogen isolation valve 90 is shut when all of the sublimed anesthetic gas is removed from cold trap/fractionator 25. The remaining nitrogen gas is flushed from cold trap/fractionator 25 through outlet 37, valve 56, and vent 46.

Second, the sublimed anesthetic gas disposed just above any liquid level at the bottom of enclosure 30 may be suctioned from cold trap/fractionator 25 and collected in tank 24C by using a vacuum pump 92. Again, the 3-way selector valve 29 is shut to isolate enclosure 30 from vent 46 and waste anesthetic gas entering from facility 10. The vacuum pump 92 draws the sublimed anesthetic gas by suction from the bottom of enclosure 30, through outlet 37, and into collection tank 24C. When all of the anesthetic gas is evacuated from cold trap/fractionator 25, the operation of vacuum pump 92 ceases and the position of selector valve 56 is reset to prevent flow to tank 24C.

Sublimed anesthetic gas may become mixed with other gases within cold trap/fractionator 25 during the thaw cycle, thereby rendering the previously described reclamation methods ineffective. Under these circumstances, additional methods, such as pressure swing adsorption, membrane separation, etc., may be employed to separate the nitrous oxide from these other gases. Various gas-gas separation techniques are well known in the prior art and will not be discussed further herein. By whichever reclamation method, the collected anesthetic gas is preferably processed for reuse.

In another embodiment of the invention, the gaseous anesthetic collection means of reclamation system 3 (FIG. 3) is incorporated in the multiple cold trap/franctionators 25A, 25B of reclamation system 2 (FIG. 2).

The Abstract of the disclosure is written solely for providing the United States Patent and Trademark Office and the public at large with a means by which to determine quickly from a cursory inspection the nature and gist of the technical disclosure, and it represents solely a preferred embodiment and is not indicative of the nature of the invention as a whole.

While some embodiments of the invention have been illustrated in detail, the invention is not limited to the embodiments shown; modifications and adaptations of the above embodiment may occur to those skilled in the art. Such modifications and adaptations are in the spirit and scope of the invention as set forth herein:

The invention claimed is:

1. A method for removing and separating a plurality of gaseous components from a waste anesthetic gas mixture comprising nitrogen, oxygen, and a plurality of halocarbons, the method comprising the steps of, cooling said waste anesthetic gas mixture by passing said gas mixture over a cooling surface (36) contained within a single enclosure, said cooling surface characterized by a surface temperature gradient such that said gas mixture passes thereover in a direction from a warmer temperature to a colder temperature, depositing by desublimation a gaseous first halocarbon component from said waste anesthetic gas mixture as a solid onto a first portion (60, 62) of said cooling surface (36), said gaseous first halocarbon component characterized by a first halocarbon melting point, said first portion (60, 62) characterized by a first temperature which is colder than said first halocarbon melting point, depositing by desublimation a gaseous second halocarbon component from said waste anesthetic gas mixture as a solid onto a second portion (63, 64) of said cooling surface (36), said gaseous second halocarbon component characterized by a second halocarbon melting point, said second portion (63, 64) characterized by a second temperature which is colder than said second halocarbon melting point and colder than said first temperature, then heating said cooling surface (36), melting said deposited second halocarbon component from said second portion (63, 64) of said cooling surface (36) into a liquid phase, then collecting said liquid second halocarbon component into a container (24A, 24B), then melting said deposited first halocarbon component from said first portion (60, 62) of said cooling surface (36) into a liquid phase, and then collecting said liquid first halocarbon component.

2. The method of claim 1 wherein, said gaseous first halocarbon component is sevoflurane and said first halocarbon melting point is a melting point of sevoflurane.

3. The method of claim 1, wherein, said gaseous second halocarbon component is isoflurane and said second halocarbon melting point is a melting point of isoflurane.

4. The method of claim 1, wherein, said gaseous second halocarbon component is desflurane and said second halocarbon melting point is a melting point of desflurane.

5. The method of claim 1 wherein, said waste anesthetic gas mixture further comprises nitrous oxide, and said method further comprises the steps of, depositing by desublimation gaseous nitrous oxide from said waste anesthetic gas mixture as a solid onto a third portion (62, 63) of said cooling surface (36), said gaseous nitrous oxide characterized by a nitrous oxide melting point, said third portion (62, 63) characterized by a third temperature which is colder than said nitrous oxide melting point, melting said deposited nitrous oxide from said third portion (62, 63) of said cooling surface (36) into a liquid phase, and collecting said liquid nitrous oxide into said container (24A, 24B).

6. The method of claim 1, further comprising the steps of, sublimating at least one halocarbon component deposited by desublimation as a solid onto said cooling surface (36) from said cooling surface (36) into a vapor phase, and then collecting said sublimed at least one halocarbon component into another container (24C).

7. The method of claim 1 further comprising the steps of, cooling said cooling surface (36) by heat transfer to and warming of a volume of liquid oxygen, then using said warmed volume of liquid oxygen in a healthcare facility (10).

8. A method for removing and separating a plurality of gaseous components from a waste anesthetic gas mixture comprising nitrogen, oxygen, and a plurality of halocarbons, the method comprising the steps of, cooling said waste anesthetic gas mixture by passing said gas mixture over a cooling surface (36) contained within a single enclosure, said cooling surface characterized by a surface temperature gradient such that said gas mixture passes thereover in a direction from a warmer temperature to a colder temperature, solidifying a gaseous first halocarbon component of said waste anesthetic gas mixture onto a first portion (60, 62) of said cooling surface (36), said gaseous first halocarbon component characterized by a first halocarbon melting point, said first portion (60, 62) characterized by a first temperature which is colder than said first halocarbon melting point, condensing a gaseous second halocarbon component of said waste anesthetic gas mixture onto a second portion (63, 64) of said cooling surface (36), said second portion (63, 64) characterized by a second temperature which is colder than said first temperature, heating said cooling surface (36), collecting said second halocarbon component as a liquid into a container (24A, 24B), melting said solidified first halocarbon component from said first portion (60, 62) of said cooling surface (36) into a liquid phase, and collecting said liquid first halocarbon component.

9. The method of claim 8, wherein, said gaseous first halocarbon component is sevoflurane and said first halocarbon melting point is a melting point of sevoflurane.

10. The method of claim 8, wherein, said gaseous second halocarbon component is isoflurane.

11. The method of claim 8, wherein, said gaseous second halocarbon component is desflurane.

12. The method of claim 8 wherein, said waste anesthetic gas mixture further comprises nitrous oxide, and said method further comprises the steps of, solidifying gaseous nitrous oxide from said waste anesthetic gas mixture onto a third portion (62, 63) of said cooling surface (36), said gaseous nitrous oxide characterized by a nitrous oxide melting point, said third portion (62, 63) characterized by a third temperature which is colder than said nitrous oxide melting point, melting said solidified nitrous oxide from said third portion (62, 63) of said cooling surface (36) into said liquid phase, and collecting said liquid nitrous oxide into said container (24A, 24B).

13. The method of claim 8 wherein, said waste anesthetic gas mixture further comprises a gaseous third anesthetic component, and said method further comprises the steps of, solidifying said gaseous third anesthetic component of said waste anesthetic gas mixture onto a third portion (62, 63, 64) of said cooling surface (36), said gaseous third anesthetic component characterized by an anesthetic melting point, said third portion (62, 63, 64) characterized by a third temperature which is colder than said anesthetic melting point, then sublimating said solidified third anesthetic component from said third portion (62, 63, 64) of said cooling surface (36) into a vapor phase, and then collecting said gaseous third anesthetic component into another container (24C).

14. The method of claim 8 further comprising the steps of, cooling said cooling surface (36) by heat transfer to and warming of a volume of liquid oxygen, then using said warmed volume of liquid oxygen in a healthcare facility (10).

15. A system for reclamation of anesthetic gas components present in waste anesthetic gas collected from an healthcare facility (10), said system comprising, a heat exchanger (25, 25A) having an inlet (31) fluidly coupled to a waste gas flow line (39), said waste gas flow line providing said waste anesthetic gas collected from said healthcare facility, said heat exchanger arranged and designed to separate anesthetic gas components from said waste anesthetic gas as said waste anesthetic gas flows through said heat exchanger between said inlet and an outlet (37) of said heat exchanger, a cooling coil (36) having an inlet and an outlet, said cooling coil positioned within said heat exchanger and having a cooling surface characterized by a surface temperature gradient such that said waste anesthetic gas passes thereover in a direction from a warmer temperature to a colder temperature, said cooling coil (36) having a first portion (60, 62) characterized by a first temperature which is colder than a first melting point of a first anesthetic component of said waste anesthetic gas, said first portion arranged and designed to desublimate said first anesthetic component of said waste anesthetic gas thereon, said cooling coil (36) also having a second portion (63, 64) characterized by a second temperature which is colder than said first temperature, said second portion arranged and designed to condense said second anesthetic component of said waste anesthetic gas thereon, containers (23, 24A, 24B, 24C) fluidly coupled to said heat exchanger, said containers arranged and designed to collect said first anesthetic component thawed from said first portion of said cooling coil and to collect said second anesthetic component condensed onto said second portion of said cooling coil, and an atmospheric discharge vent (46) fluidly coupled to said outlet of said heat exchanger, said atmospheric discharge vent discharging said waste anesthetic gas without said first and second anesthetic components to atmosphere.

16. The system of claim 15 further comprising, another heat exchanger (25B) having an inlet (31) fluidly coupled to said waste gas flow line (39), said waste gas flow line providing said waste anesthetic gas collected from said healthcare facility, said another heat exchanger arranged and designed to separate anesthetic gas components from said waste anesthetic gas as said waste anesthetic gas flows through said another heat exchanger between said inlet and an outlet (37) of said another heat exchanger, another cooling coil (36) having an inlet and an outlet, said another cooling coil positioned within said another heat exchanger and having a cooling surface characterized by a surface temperature gradient such that said waste anesthetic gas passes thereover in a direction from a warmer temperature to a colder temperature, said another cooling coil (36) having a first portion (60, 62) characterized by a first temperature which is colder than said first melting point of said first anesthetic component of said waste anesthetic gas, said first portion arranged and designed to desublimate said first anesthetic component of said waste anesthetic gas thereon, said another cooling coil (36) also having a second portion (63, 64) characterized by a second temperature which is colder than said first temperature, said second portion arranged and designed to condense said second anesthetic component of said waste anesthetic gas thereon, and wherein, said containers are fluidly coupled to said another heat exchanger, said containers arranged and designed to collect said first anesthetic component thawed from said first portion of said another cooling coil and to collect said second anesthetic component condensed onto said second portion of said another cooling coil, and said atmospheric discharge vent is fluidly coupled to said outlet of said another heat exchanger, whereby when said waste anesthetic gas flows through said heat exchanger, said another cooling coil of said another heat exchanger is thawed and when said waste anesthetic gas flows through said another heat exchanger, said cooling coil of said heat exchanger is thawed.

17. The system of claim 15 further comprising, a source (20) of liquid oxygen fluidly coupled to said inlet of said cooling coil, said source arranged and designed to pass liquid oxygen through said cooling coil from said inlet to said outlet.

18. The system of claim 15 further comprising, a source (20) of liquid nitrogen fluidly coupled to said inlet of said cooling coil, said source arranged and designed to pass liquid nitrogen through said cooling coil from said inlet to said outlet.

19. The system of claim 15 further comprising, a vacuum pump (92) in fluid communication with said outlet of said heat exchanger, said vacuum pump arranged and designed to draw any sublimed gas from said heat exchanger into one of said containers.

20. The system of claim 15 further comprising, a source (89) of nitrogen gas fluidly coupled to said heat exchanger, said source arranged and designed to pass nitrogen through said heat exchanger to force any sublimed anesthetic components into one of said containers.

* * * * *

UNITED STATES PATENT AND TRADEMARK OFFICE
CERTIFICATE OF CORRECTION

PATENT NO. : 7,596,965 B2
APPLICATION NO. : 11/432189
DATED : October 6, 2009
INVENTOR(S) : Berry et al.

Page 1 of 5

It is certified that error appears in the above-identified patent and that said Letters Patent is hereby corrected as shown below:

The title page, showing an illustrative figure, should be deleted and substitute therefor the attached title page.

Delete drawing sheets 1-3 and substitute therefor the drawing sheets, consisting of figures 1-3 as shown on the attached pages.

Signed and Sealed this

Thirty-first Day of August, 2010

David J. Kappos
*Director of the United States Patent and Trademark Office*

(12) United States Patent
Berry et al.

(10) Patent No.: US 7,596,965 B2
(45) Date of Patent: Oct. 6, 2009

(54) ANESTHETIC GAS RECLAMATION SYSTEM AND METHOD

(75) Inventors: James M. Berry, Nashville, TN (US); Steve Morris, Canton, MS (US)

(73) Assignee: Anesthetic Gas Reclamation, LLC, Nashville, TN (US)

(*) Notice: Subject to any disclaimer, the term of this patent is extended or adjusted under 35 U.S.C. 154(b) by 319 days.

(21) Appl. No.: 11/432,189

(22) Filed: May 11, 2006

(65) Prior Publication Data
US 2006/0254587 A1 Nov. 16, 2006

Related U.S. Application Data

(60) Provisional application No. 60/680,644, filed on May 13, 2005, provisional application No. 60/682,249, filed on May 18, 2005.

(51) Int. Cl.
- B01D 9/04 (2006.01)
- F25J 3/00 (2006.01)
- F24F 5/00 (2006.01)
- A62B 7/00 (2006.01)

(52) U.S. Cl. ............... 62/532; 62/617; 62/637; 128/204.16; 128/205.12

(58) Field of Classification Search ............ 62/637, 62/617, 532; 128/200.24, 204.16, 203.25, 128/205.12; 423/235
See application file for complete search history.

(56) References Cited
U.S. PATENT DOCUMENTS

| | | |
|---|---|---|
| 575,714 A | 1/1897 | Heinzerling |
| 1,040,886 A | 10/1912 | Claude |

(Continued)

FOREIGN PATENT DOCUMENTS

WO  WO 98/08583  3/1998

(Continued)

OTHER PUBLICATIONS

R. F. Dunn, M. Zhu, B.K. Srinivas and M. M. El-Halwagi (1995), Optimal Design of Energy-Induced Separation Networks for VOC Recovery, *AIChE Symp. Ser.*, 90(303), 74-85, NY: AIChE.

(Continued)

*Primary Examiner*—William C Doerrler
(74) *Attorney, Agent, or Firm*—Gary L. Bush; Mark D. Shelley, II; Andrews Kurth LLP (57) ABSTRACT

A method and system for the fractionation and removal of nitrous oxide and other volatile halocarbon gas components from waste anesthetic gases using liquid oxygen are disclosed. Liquid oxygen is warmed for use in a healthcare facility by cooling and condensing waste anesthetic gases. A cold trap/fractionator is provided wherein selective components of the waste anesthetic gas are collected as a frost on the coils of the cold trap/fractionator by desublimation/deposition and/or condensation/solidification. In a periodic batch process, the collected frost is first thawed and the melted liquids or gases are then collected at various increasing temperatures, thereby separating the nitrous oxide and other halocarbon gas components by their varying melting points. The thawed anesthetic components are collected in separate tanks based on their melting points. Warmed by the waste anesthetic gases in the cold trap/fractionator, the oxygen is supplied to the healthcare facility for its normal uses.

20 Claims, 3 Drawing Sheets